US012433983B2

(12) United States Patent
Jeyachandran et al.

(10) Patent No.: US 12,433,983 B2
(45) Date of Patent: Oct. 7, 2025

(54) ONLINE FLUID GENERATING PERITONEAL DIALYSIS CYCLER

(71) Applicants: BAXTER INTERNATIONAL INC., Deerfield, IL (US); BAXTER HEALTHCARE SA, Glattpark (CH)

(72) Inventors: Ramkumar Jeyachandran, Bangalore (IN); Anders J. Wellings, Belleair Beach, FL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 0 days.

(21) Appl. No.: 18/568,476

(22) PCT Filed: Jun. 1, 2022

(86) PCT No.: PCT/US2022/031775
§ 371 (c)(1),
(2) Date: Dec. 8, 2023

(87) PCT Pub. No.: WO2022/260904
PCT Pub. Date: Dec. 15, 2022

(65) Prior Publication Data

US 2024/0269363 A1 Aug. 15, 2024

(30) Foreign Application Priority Data

Jun. 8, 2021 (IN) ............................ 202141025465

(51) Int. Cl.
*A61M 1/28* (2006.01)

(52) U.S. Cl.
CPC ..... *A61M 1/282* (2014.02); *A61M 2205/3317* (2013.01); *A61M 2205/3337* (2013.01)

(58) Field of Classification Search
CPC .... A61M 1/168; A61M 1/1688; A61M 1/169; A61M 1/28; A61M 1/281; A61M 1/282;
(Continued)

(56) References Cited

U.S. PATENT DOCUMENTS

2017/0281847 A1 10/2017 Venkatesh et al.
2019/0125954 A1 5/2019 Mathiot
2019/0358387 A1* 11/2019 Elbadry ................ A61M 1/361

OTHER PUBLICATIONS

International Search Report; PCT/US2022/031775 mailing date Sep. 9, 2022—3 pages.

(Continued)

*Primary Examiner* — Kami A Bosworth
(74) *Attorney, Agent, or Firm* — K&L Gates LLP

(57) ABSTRACT

A peritoneal dialysis ("PD") machine includes a water pump; a concentrate pump; a water valve, and an inlet to the water valve positioned to receive purified water; a concentrate valve, and an inlet to the concentrate valve positioned to receive PD fluid concentrate; a mixing line located downstream from the water pump and the a concentrate pump; a conductivity sensor positioned to sense mixed purified water and PD fluid concentrate that form fresh PD fluid; a flexible patient line configured to bring fresh PD fluid to and remove used PD fluid from a patient; and a control unit configured to control the water pump, the concentrate pump, the water valve and the concentrate valve, to receive an output from the conductivity sensor, and to run a disinfection sequence in which (i) the inlet to the concentrate valve alternatively receives disinfectant or (ii) the flexible patient line alternatively receives disinfectant.

20 Claims, 5 Drawing Sheets

(58) Field of Classification Search
CPC ...... A61M 1/284; A61M 1/287; A61M 1/288; A61L 2/18; A61L 2/183; A61L 2/186; A61L 2/24
See application file for complete search history.

(56) References Cited

OTHER PUBLICATIONS

Written Opinion of the International Searching Authority mailing date Sep. 9, 2022—8 pages.
International Preliminary Report on Patentability dated Aug. 8, 2023—7 pages.

* cited by examiner

ONLINE FLUID GENERATING PERITONEAL DIALYSIS CYCLER

PRIORITY CLAIM

The present application is a national phase entry of PCT Patent Application No. PCT/US2022/031775, filed on Jun. 1, 2022, which claims priority to and the benefit of Indian Provisional Patent Application No. 202141025465, filed on Jun. 8, 2021, the entire contents of which are incorporated herein by reference and relied upon.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal cavity, though the catheter, and to the drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

Known automated peritoneal dialysis ("PD") systems typically include a machine or cycler that accepts and actuates a pumping cassette having a hard part and a soft part that is deformable for performing pumping and valving operations. The hard part is attached to tubes that extend to various bags. The disposable cassette and associated tubes and bags can be cumbersome for a patient at home to load for treatment. The overall amount of disposable items may also lead to multiple setup procedures requiring input from the patient, which can expose room for error.

In a first main feature of the present disclosure, the APD system and associated methodology generates fresh PD fluid online at the time of treatment. This feature allows for smaller concentrate containers to be used instead of requiring the containers to hold an entire treatment volume. The PD machine or cycler is valved and includes connections for connecting to a source of purified water and at least one source of PD fluid concentrate. In an embodiment, first and second primary sources of PD fluid concentrates are provided along with a source of last fill fluid. First and second valves are provided, one each for the first and second primary sources of PD fluid concentrates. A concentrate pump is positioned to pump from either of the first and second sources of PD fluid concentrates. The first and second valves determine which of the first and second sources of PD fluid concentrates currently supplies concentrate to the concentrate pump. The first and second concentrates may be the same and may include each of the constituent concentrates needed to form a finally prepared PD fluid. For example, the first and second concentrates may each include a glucose concentrate and an electrolyte concentrate that are provided in separate chambers divided by a peel seal that the patient opens at the beginning of treatment. The glucose and electrolyte mixture is then further mixed with purified water to form finally prepared PD fluid.

In an alternative embodiment, the first and second concentrates each include one of the constituent concentrates, for example, one concentrate may include glucose while the other includes electrolyte. Here, purified water is mixed with the glucose concentrate and the electrolyte concentrate from the two sources to form finally prepared PD fluid. In this alternative, the finally prepared PD fluid may be mixed somewhere in the cycler or in the patient.

A source of last fill fluid may also be provided in addition to the first and second PD fluid concentrates. The last fill fluid may be fully prepared and not mixed with purified water. Alternatively, the last fill fluid may be a last fill concentrate, which is mixed with purified water to form finally mixed last fill PD fluid, e.g., icodextrine. The PD machine or cycler in an embodiment provides a separate valve to allow last fill fluid to be pumped by the concentrate pump at the end of treatment.

A separate valve may be provided for the source of purified water to selectively allow purified water to be supplied in an amount needed to produce finally mixed PD fluid for treatment. The source of purified water may include one or more container of purified water or an online water purification unit, which generates purified water from tap water provided at the patient's home or dwelling. A separate water pump may be provided for pumping the purified water so that PD fluid concentrate and purified water can be dosed and controlled independently.

A mixer, such as a static mixer, is located downstream of the water and concentrate pumps to homogeneously mix the purified water and PD fluid concentrate. A first conductivity sensor is located downstream from the mixer to test the mixture and provide feedback for controlling the water and concentrate pumps to produce a prescribed final PD fluid. A fresh PD fluid flow sensor, inline heater, temperature sensor and second conductivity sensor may be provided in a desired order downstream from the first conductivity sensor. The inline heater operates with the temperature sensor to heat the mixed PD fluid to a desired patient temperature for treatment, e.g., 37° C. The second conductivity sensor may be used to provide a safety or redundancy check on the composition of the PD fluid and be located just upstream from a bypass line allowing any improperly mixed PD fluid to be diverted instead to drain.

In an embodiment, a fresh PD fluid pressure sensor and a final or sterile stage filter are provided in a fresh PD fluid line near the exit of the machine or cycler to the patient. The fresh PD fluid pressure sensor provides feedback so that a positive patient pressure limit is not exceeded when filling the patient. The final or sterile stage filter may be a semi-reusable filter, such as an ultrafilter, which may be replaced every few months or so. The final or sterile stage filter provides a final sterilization step for the PD fluid, which serves as a check against any pathogens that may remain after the disinfection discussed below.

In an embodiment, the internal patient line having the fresh PD fluid pressure sensor and final or sterile stage filter extends to a "Y" or "T" connector. A flexible patient line extends from the "Y" or "T" connector to the patient's transfer set and indwelling catheter. A used dialysis fluid line extends from the other leg or port of the "Y" or "T" connector and includes, in some order, a used PD fluid pressure sensor, a used PD fluid conductivity sensor, a used PD fluid flow sensor and a used dialysis fluid pump. The used dialysis fluid line eventually leads to a drain, such as a drain container or a house drain.

The used PD fluid pressure sensor provides feedback so that a negative patient pressure limit is not exceeded when draining the patient. The output from the used PD fluid conductivity sensor may be used to interrogate the used dialysis fluid or patient effluent to look for solute removal in the patient's effluent (e.g., for urea, $\beta_2$ microglobulin, and/or creatinine) or for signs of peritonitis. The outputs from the fresh and used flow sensors may be used to set fresh and used PD fluid flowrates and may also be integrated over time to yield (i) how much fresh dialysis fluid is delivered to the patient, (ii) how much used dialysis fluid is removed from the patient, and (iii) a difference between (ii) versus (i) to know how much ultrafiltration ("UF") or excess water has been removed from the patient.

Any of the pumps, including the water pump, the concentrate pump and the used dialysis fluid pump, may be peristaltic, piston, gear, membrane or centrifugal pumps and have reusable components that contact fresh and used PD fluid over many treatments. The valves may be two-way or three-way valves that likewise have reusable components that contact fresh and used PD fluid over many treatments. A control unit is provided that controls the pumps and valves and that receives outputs from each of the sensors discussed herein, which may be used as feedback to control the pumps and valves.

In various embodiment, the cycler includes varying numbers of concentrate sources and associated valves. For example, a single primary source of concentrate may be provided along with a last fill source of fluid, wherein the single primary source of concentrate is sized to hold enough PD fluid concentrate (glucose and electrolyte) to form multiple, e.g., three or more, patient fills worth of final PD fluid (a patient fill may be on the order of one to three liters). In another alternative embodiment, the internal patient line discussed above as being dedicated to delivering fresh PD fluid may be reconfigured to handle both fresh and used PD fluid in a two-way manner. The reconfigured patient line enables multiple valves and sensors to be eliminated, simplifying the overall system.

In a second main feature of the present disclosure, the APD system and associated methodology provides much of the fluid lines and components as reusable lines and components, e.g., having no disposable parts, which lowers disposable cost, waste and handling. The reusable lines and components are then disinfected after treatment, e.g., chemical and heat disinfected. The reusable components may include all pumps, valves and sensors. The final or sterile stage filter as discussed herein may be reused for multiple treatments and then replaced periodically. All internal fluid lines may be reusable along with the flexible patient line and a flexible portion of the used PD fluid or drain line.

In one sterilization embodiment, the sources of PD fluid concentrate are removed after treatment and are replaced by a source of disinfectant, e.g., citric acid. The flexible patient line and the flexible portion of the used PD fluid or drain line are connected together to form a closed disinfection circuit or pathway. Any one or more of the pumps then circulates citric acid disinfectant, which may be concentrated and combined with purified water, around the closed disinfection circuit or pathway, perhaps in multiple directions, while the heater heats the disinfectant to a desired temperature, e.g., 70° C. to 90° C., and while any one or more of the valves is toggled so that each line and component is sufficiently contacted. A reusable and portable drain container may be provided that allows any remaining fresh or used PD fluid after treatment to be removed from the cycler to allow the disinfectant is introduced into the cycler for disinfection. The reusable and portable drain container also allows the disinfectant to be removed from the cycler to allow fresh PD fluid to prime the cycler before the next treatment. Either of these operations may include a purified water rinse from the source of purified water and/or a filtered air purge.

In another sterilization embodiment, the sources of PD fluid concentrate are left in place after treatment, while the flexible patient line is attached to the source of disinfectant, e.g., citric acid. The flexible portion of the used PD fluid or drain line may be left in place extending to a drain container or house drain. Any one or more of the pumps then circulates citric acid disinfectant, which may be concentrated and combined with purified water, around a closed disinfection circuit or pathway (sealed closed using relevant valves), perhaps in multiple directions, while the heater heats the disinfectant to a desired temperature, e.g., 70° C. to 90° C., and while any one or more of the valves not used to seal the disinfection loop closed is toggled so that each line and component is sufficiently contacted. At the end of the second sterilization embodiment, the disinfectant is pumped to drain (container or house) and is backfilled with (i) purified water and/or filtered air (e.g., prior to the start of the next treatment) or (ii) fresh PD fluid for priming at the start of the next treatment.

In light of the disclosure set forth herein, and without limiting the disclosure in any way, in a first aspect of the present disclosure, which may be combined with any other aspect or portion thereof, a peritoneal dialysis ("PD") machine includes a water pump: a concentrate pump: a water valve located upstream of the water pump, and an inlet to the water valve positioned to receive purified water: a concentrate valve located upstream of the concentrate pump, and an inlet to the concentrate valve positioned to receive PD fluid concentrate: a mixing line located downstream from the water pump and the concentrate pump: a conductivity sensor positioned to sense mixed purified water and PD fluid concentrate that at least partially form fresh PD fluid: a flexible patient line configured to bring at least partially formed fresh PD fluid to and remove used PD fluid from a patient; and a control unit configured to control the water pump, the concentrate pump, the water valve and the concentrate valve, the control unit also configured receive an output from the conductivity sensor, the control unit further configured to run a disinfection sequence in which (i) the inlet to the concentrate valve instead receives disinfectant or (ii) the flexible patient line instead receives disinfectant.

In a second aspect of the present disclosure, which may be combined with any other aspect or portion thereof, the PD machine further includes a used PD fluid line, and wherein during (i) the flexible patient line is placed in fluid communication with the used PD fluid line, or during (ii) the used PD fluid line is placed in fluid communication with a drain container or house drain.

In a third aspect of the present disclosure, which may be combined with any other aspect or portion thereof, during treatment the used PD fluid line is placed in fluid communication with the drain container or house drain.

In a fourth aspect of the present disclosure, which may be combined with any other aspect or portion thereof, the drain container is a reusable container.

In a fifth aspect of the present disclosure, which may be combined with any other aspect or portion thereof, the PD machine includes a used dialysis fluid pump operable with the used PD fluid line.

In a sixth aspect of the present disclosure, which may be combined with any other aspect or portion thereof, at least one of the water pump, the concentrate pump or the used dialysis fluid pump is operated in at least one direction during (i) or (ii).

In a seventh aspect of the present disclosure, which may be combined with any other aspect or portion thereof, the PD machine includes a final or sterile stage filter positioned and arranged to filter fresh PD fluid prior to delivery to the patient.

In an eighth aspect of the present disclosure, which may be combined with any other aspect or portion thereof, the final or sterile stage filter is at least one of reusable or an ultrafilter.

In a ninth aspect of the present disclosure, which may be combined with any other aspect or portion thereof, the PD machine includes a mixer, optionally a static mixer, located along the mixing line.

In a tenth aspect of the present disclosure, which may be combined with any other aspect or portion thereof, the PD machine includes a heater, and wherein the control unit is further configured to cause the heater to heat the disinfectant during the disinfection sequence.

In an eleventh aspect of the present disclosure, which may be combined with any other aspect or portion thereof, the heater is an inline heater.

In a twelfth aspect of the present disclosure, which may be combined with any other aspect or portion thereof, the PD includes an internal patient line positioned (a) to deliver fresh dialysis fluid to the flexible patient line, wherein a used dialysis fluid line receives used dialysis fluid from the flexible patient line, or (b) to deliver fresh dialysis fluid to the flexible patient line and receive used dialysis fluid from the flexible patient line.

In a thirteenth aspect of the present disclosure, which may be combined with any other aspect or portion thereof, in (a) a fresh PD fluid pressure sensor is operable with the internal patient line and a used PD fluid pressure sensor is operable with the used dialysis fluid line, or in (b) a fresh and used PD fluid pressure sensor is operable with the internal patient line.

In a fourteenth aspect of the present disclosure, which may be combined with any other aspect or portion thereof, in (a) the conductivity sensor is operable with the mixing line and a second conductivity sensor is operable with the used dialysis fluid line, or in (b) the conductivity sensor is operable with the mixing line and a second conductivity sensor is operable with the internal patient line.

In a fifteenth aspect of the present disclosure, which may be combined with any other aspect or portion thereof, the control unit is configured use the output from the conductivity sensor for feedback in mixing the mixed purified water and PD fluid concentrate and the output from the second conductivity sensor for evaluating used dialysis fluid removed from the patient.

In a sixteenth aspect of the present disclosure, which may be combined with any other aspect or portion thereof, in (a) a first flow sensor is operable with the mixing line or the internal patient line and a second flow sensor is operable with the used dialysis fluid line, or in (b) a first flow sensor is operable with the mixing line and a second flow sensor is operable with a used dialysis fluid line, or in (b) a single flow sensor is operable with the internal patient line.

In a seventeenth aspect of the present disclosure, which may be combined with any other aspect or portion thereof, the control unit is configured to use outputs from the first and second flow sensors or the single flow sensor to at least one of (a) control a fresh PD fluid flowrate, (b) control a used PD fluid flowrate, (c) determine an amount of fresh PD fluid delivered to the patient, (d) determine an amount of used PD fluid removed from the patient, or (e) determine an amount of ultrafiltration ("UF") removed from the patient.

In an eighteenth aspect of the present disclosure, which may be combined with any other aspect or portion thereof, the control unit is configured to cause a performance of at least one of (a) a purified water rinse of residual fresh and/or used dialysis fluid prior to introduction of the disinfectant, (b) a rinse of residual fresh and/or used dialysis fluid using the disinfectant, (c) a purified water rinse of the disinfectant after the disinfection sequence, or (d) a filtered air purge after the disinfection sequence.

In a nineteenth aspect of the present disclosure, which may be combined with any other aspect or portion thereof, the concentrate valve is a first concentrate valve and the PD concentrate is a first PD concentrate, and which includes a second concentrate valve under control of the control unit, the second concentrate valve located upstream of the concentrate pump, and an inlet to the second concentrate valve positioned to receive a second PD fluid concentrate, and wherein the control unit is further configured to manipulate the first and second concentrate valves and control the concentrate pump so as to (i) mix the first concentrate or the second concentrate with purified water or (ii) mix the first concentrate and the second concentrate with purified water.

In a twentieth aspect of the present disclosure, which may be combined with any other aspect or portion thereof, in (ii) final fresh PD fluid is mixed in the mixing line or in the patient.

In a twenty-first aspect of the present disclosure, which may be combined with any other aspect or portion thereof, a peritoneal dialysis ("PD") system includes a source of purified water: a source of PD fluid concentrate; and a PD machine including a water pump for pumping purified water, a concentrate pump for pumping PD fluid concentrate, a water valve located upstream of the water pump: a concentrate valve located upstream of the concentrate pump, a mixing line located downstream from the water pump and the concentrate pump, a conductivity sensor positioned to sense mixed purified water and PD fluid concentrate that at least partially form fresh PD fluid, a flexible patient line configured to bring at least partially formed fresh PD fluid to and remove used PD fluid from a patient, and a control unit configured to control the water pump, the concentrate pump, the water valve and the concentrate valve, the control unit also configured receive an output from the conductivity sensor, the control unit further configured to run a disinfection sequence in which (i) the inlet to the concentrate valve instead receives disinfectant or (ii) the flexible patient line instead receives disinfectant.

In a twenty-second aspect of the present disclosure, which may be combined with any other aspect or portion thereof, the source of purified water includes one or more containers or bags of purified water or an online water purification unit.

In a twenty-third aspect of the present disclosure, which may be combined with any other aspect or portion thereof, the source of PD fluid concentrate includes a dual chamber container including separate glucose and electrolyte concentrates.

In a twenty-fourth aspect of the present disclosure, which may be combined with any other aspect or portion thereof, any of the features, functionality and alternatives described in connection with any one or more of FIGS. 1 to 5 may be combined with any of the features, functionality and alternatives described in connection with any other of FIGS. 1 to 5.

It is accordingly an advantage of the present disclosure to provide a relatively volumetrically accurate automated peritoneal dialysis ("APD") machine or cycler.

It is another advantage of the present disclosure to provide an APD cycler that achieves relatively precise pressure control.

It is yet another advantage of the present disclosure to provide an APD cycler that is capable of mixing peritoneal dialysis ("PD") fluid online at the time of use.

It is still another advantage of the present disclosure to provide an APD cycler that is capable of capable of varying glucose and electrolyte PD fluid concentrations to suit a particular patient's needs.

Further still, it is an advantage of the present disclosure to provide an APD cycler that reduces disposable cost by replacing fully prepared dialysis fluid containers (e.g., one to six liters) with smaller concentrate containers.

It is a further advantage of the present disclosure to provide a relatively quiet APD cycler.

It is yet a further advantage of the present disclosure to provide an APD cycler that disinfects components after treatment, further allowing disposable waste and cost to be reduced, e.g., by allowing a disposable heating component to be eliminated.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description.

Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

First Cycler Embodiment

Figure 1:
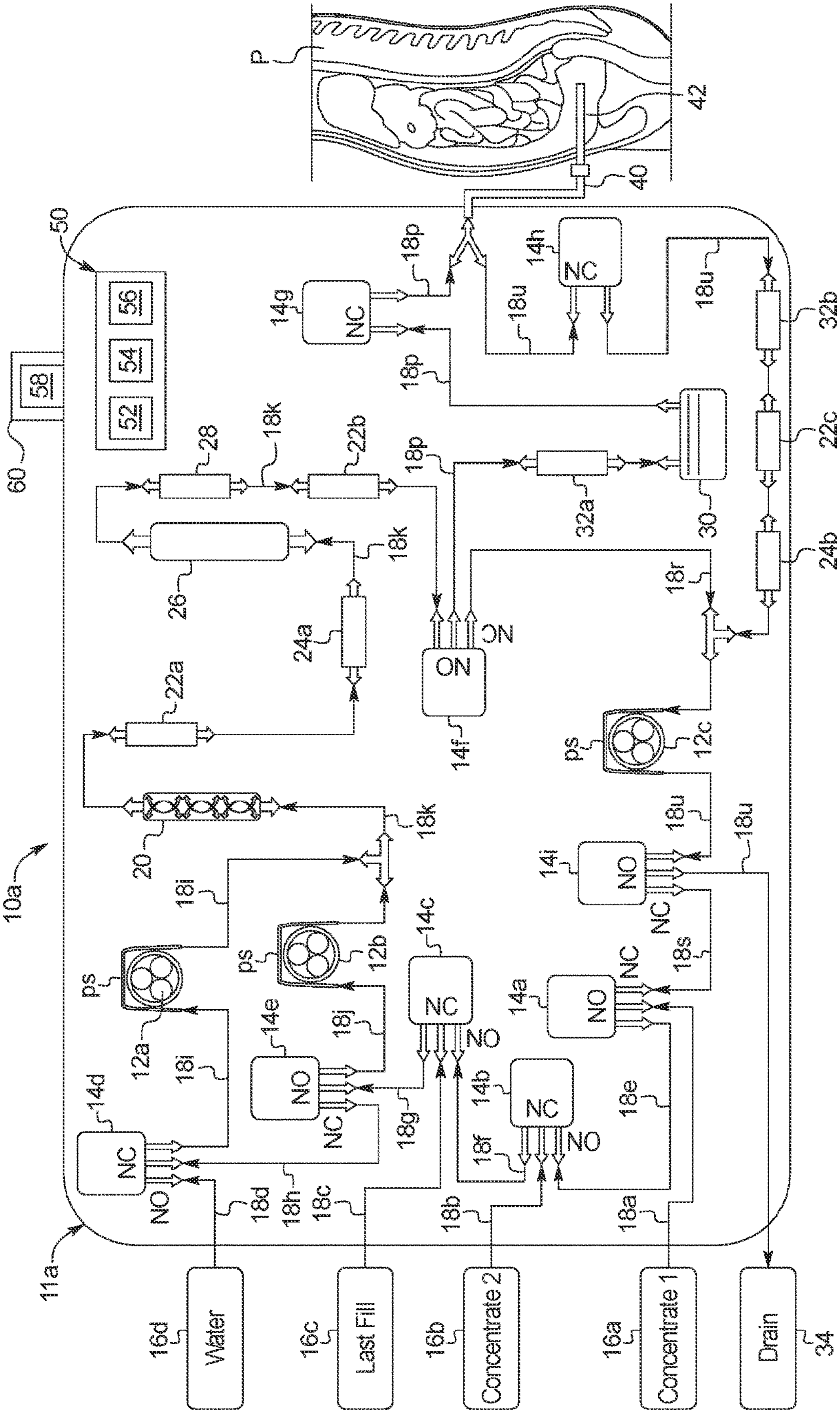
FIG. 1 is a flow schematic view of a first automated peritoneal dialysis ("APD") system of the present disclosure having online dialysis fluid generation using multiple concentrate sources and post-treatment disinfection.

Referring now to the drawings and in particular to FIG. 1, a first primary embodiment of an automated peritoneal dialysis ("APD") system 10*a* and associated methodology of the present disclosure includes an APD machine or cycler 11*a*, which is generally defined by the rectangular box in FIG. 1. In the illustrated embodiment, APD machine or cycler 11*a* includes water and concentrate pumps 12*a* and 12*b*, respectively, and a used dialysis fluid pump 12*c*. Pumps 12*a* to 12*c* are illustrated as peristaltic pumps, however, pumps 12*a* to 12*c* may be any type of fluid pump, for example, a piston, gear, membrane or centrifugal pump, and may be of the same type or different types. Due to the reusable nature of system 10*a*, pumps 12*a* to 12*c* are not limited to types that operate with a disposable item, such as a tube or a flexible chamber. Pumps 12*a* to 12*c* instead may include or define internal, e.g., metallic or partially metallic, cavities that receive and contact a fluid to be pumped, such as fresh or used dialysis fluid. On the other hand, pumps 12*a* to 12*c* may be peristaltic or membrane pumps that operate with a tube, flexible chamber, or other flexible fluid contacting portion that would in other circumstances be disposable, but which here are disinfected after treatment or prior to a subsequent treatment for reuse.

Cycler 11*a* of system 10*a* includes a first concentrate valve 14*a*, a second concentrate valve 14*b* located downstream from first concentrate valve 14*a*, a last fill valve 14*c* located downstream from second concentrate valve 14*b*, a water valve 14*d* located downstream from last fill valve 14*c*, and a fresh, upstream valve 14*e* located between last fill valve 14*c* and water valve 14*d*. Valves 14*a* to 14*e* are electrically actuated three-way valves in the illustrated embodiment, each including a normally open ("NO") port, a normally closed ("NC") port and a common port. When energy is applied to valves 14*a* and 14*e* (and each of the three-way valves described herein), the ports switch states such that the NO port closes (restricts flow to the common port) and the NC port opens (allows flow to the common port). Due to the reuse of system 10*a* and the other systems described herein, any of the valves described herein, including valves 14*a* to 14*e*, may include internal fluid contacting portions that are metallic or otherwise of a nature that would be cost prohibitive to discard after each treatment. In alternative embodiments, any of the valves described herein may operate with tubing (e.g., pinch valves) or flexible membranes (e.g., electric or pneumatic volcano valves), which are disinfected after treatment and reused. In still further alternative embodiments, any of the three-way valves described herein, including valves 14*a* to 14*e*, may be replaced via multiple two-way valves.

First concentrate valve 14*a* is communicated fluidly with a first source of concentrate 16*a* via a first concentrate line 18*a*. Second concentrate valve 14*b* is communicated fluidly with a second source of concentrate 16*b* via a second concentrate line 18*b*. Last fill valve 14*c* is communicated fluidly with a source of last fill fluid 16*c*, e.g., icodextrine, via a last fill line 18*c*. Water valve 14*d* is communicated fluidly with a source of purified water 16*d* via a water line 18*d*. First concentrate valve 14*a* and second concentrate valve 14*b* are communicated fluidly via line 18*e*. Second concentrate valve 14*b* and last fill valve 14*c* are communicated fluidly via line 18*f*. Last fill valve 14*c* and fresh, upstream valve 14*e* are communicated fluidly via line 18*g*. Fresh, upstream valve 14*e* and water valve 14*d* are communicated fluidly via line 18*h*.

First and second concentrates 16*a* and 16*b* may be the same or different than each other and may each hold a single or multiple patient fills worth of concentrate. First and second concentrate sources 16*a* and 16*b* may each include all concentrates needed to form PD fluid such that once properly mixed with purified water, a ready to use PD fluid is formed. For example, first and second concentrate sources 16*a* and 16*b* may each include an electrolyte concentrate and a glucose concentrate, which may be separated from each other prior to treatment in dual chambers or pouches divided by a peel seal. At the time of treatment, the patient or caregiver opens the peel seal to allow the different concentrates to mix with each other before being combined with purified water. In an alternative embodiment, first and second concentrate sources 16*a* and 16*b* each only include a single concentrate, e.g., first concentrate source 16*a* holds electrolyte, while second concentrate source holds glucose. Here, both concentrates 16*a* and 16*b* are initially mixed with water and are finally mixed either at a static mixer 20 or at patient P. As used herein, an electrolyte solution also includes a buffer solution.

Source of last fill fluid 16*c* may be a finally mixed last fill PD fluid, e.g., icodextrin, which is not further mixed with purified water from purified water source 16*d*. Source of last fill fluid 16*c* may alternatively be a last fill concentrate, e.g., icodextrin concentrate, which is further mixed with purified water from purified water source 16*d*. Purified water source 16*d* may include one or more containers or bags of purified water or be an online water purification unit, such as a WRO 300 unit made by the assignee of the present disclosure.

In FIG. 1, water valve 14*d* communicates fluidly with water pump line 18*i*, which operates with water pump 12*a*. Fresh, upstream valve 14*e* communicates fluidly with concentrate pump line 18*j*, which operates with concentrate pump 12*b*. Water pump line 18*i* and concentrate pump line 18*j* in the illustrated embodiment (and the same for used dialysis fluid pump 12c) include a thickened, flexible pumping section ps, which may be of a desirable material type and shore hardness for peristaltic pumping. Water pump line 18i and concentrate pump line 18j "T" or "Y" together at a mixing line 18k ahead of static mixer 20. Static mixer 20 in one embodiment includes metal (e.g., stainless steel, steel or aluminum and/or plastic (e.g., polyvinyl chloride ("PVC"), polyethylene ("PE"), polyurethane ("PU") and/or polycarbonate ("PC")) baffles or blades that turbulate and mix purified water with one or more concentrate 16a, 16b or last fill concentrate 16c to form a fully or partially mixed PD fluid. Static mixer 20 and its baffles or blades in an embodiment are made to be durable and reusable.

Mixing line 18k in the illustrated embodiment of FIG. 1 also includes a first conductivity sensor 22a, fresh PD fluid flow sensor 24a, inline heater 26, temperature sensor 28 and second conductivity sensor 22b. Conductivity sensors 22a and 22b (and any described herein) may be inline, durable, and temperature compensated conductivity sensors, such as temperature compensated graphite probes. Flow sensor 24a (and any flow sensors described herein) may be inline, durable and in one example magnetic flow sensors. Other suitable invasive flow sensors include rotary vane, vortex shedding, optical, and mass flow sensors for example. Non-invasive flow sensors may also be provided and include heat pulse, time of flight and optical flow sensors, for example. Inline heater 26 is durable in one embodiment and is configured so as to be able to heat fully or partially mixed PD fluid from, e.g., 10° C. to body temperature or 37° C. over flowrates ranging from, e.g., 50 ml/min to 300 ml/min. Inline heater 26 may include a flow through and/or circulation heater. Temperature sensor 28 may be a thermocouple or thermistor for example.

Mixing line 18k extends to three-way fresh, downstream valve 14f. An internal fresh PD fluid patient line 18p extends from fresh, downstream valve 14f to a semi-reusable final or sterile stage filter 30. Semi-reusable final or sterile stage filter 30 may for example be an ultrafilter, which is reusable for a number of uses or service hours after which it is replaced by a service person, patient or caregiver depending on its location and connection to cycler 11a. Semi-reusable final or sterile stage filter 30 may for example be configured with self-sealing quick disconnect connectors that allow the filter to be easily plugged into and removed from a readily accessible surface or cavity of cycler 11a. Semi-reusable final or sterile stage filter 30 is configured to make the finally or partially mixed PD fluid of an injectable quality for delivery to patient P.

A fresh PD fluid pressure sensor 32a may be located along internal fresh PD fluid patient line 18p upstream or downstream of final or sterile stage filter 30. Fresh PD fluid pressure sensor 32a (and any pressure sensor described herein) may be a pod-type pressure sensor having a flexible diaphragm separating a fluid contacting side and an air side leading to a pressure transducer. Alternatively, fresh PD fluid pressure sensor 32a (and any pressure sensor described herein) may be a force sensor that abuts directly against a flexible portion of internal patient line 18p. Further alternatively, fresh PD fluid pressure sensor 32a (and any pressure sensor described herein) may be a durable, invasive, inline pressure sensor through which fresh PD fluid (or other) flows.

Fresh PD fluid patient line 18p includes a fresh PD fluid patient valve 14g, which may be a two-way valve that either allows or prevents fresh, heated and properly sterilized PD fluid to flow through a flexible patient line 40 (which may be reusable) and indwelling patient catheter 42 into the patient P's peritoneal cavity, where the PD fluid is allowed to dwell for a specified duration. In the illustrated embodiment, fresh PD fluid patient valve 14g connects to flexible patient line 40 via a "T" or "Y" connector. The other leg of the "T" or "Y" connector connects to used dialysis fluid line 18u.

A used PD fluid patient valve 14h is located along used dialysis fluid line 18u and may also be a two-way valve that either allows or prevents used PD fluid to be pulled via used dialysis pump 12c from patient P's peritoneal cavity, through indwelling patient catheter 42 and flexible patient line 40, into used dialysis fluid line 18u. In the illustrated embodiment, used dialysis fluid line 18u includes for operates with used PD fluid flow sensor 24b, used PD fluid conductivity sensor 22c, and used PD fluid pressure sensor 32b. Used dialysis pump 12c pumps used dialysis fluid from patient P along used dialysis fluid line 18u to a drain 34, which may be a drain container or bag or a house drain such as a toilet, bathtub or sink.

Cycler 11a also includes first and second recirculation lines 18r and 18s, which allow various fluids discussed herein to be recirculated throughout the cycler instead of being delivered to drain. First recirculation line 18r extends from an alternative destination port of three-way fresh, downstream valve 14f to a "T" or "Y" connection with used dialysis fluid line 18u at an inlet to used dialysis pump 12c (or outlet from if pump is reversed). A recirculation valve 14i is provided to allow used dialysis fluid to flow through used dialysis fluid line 18u to drain 34 or some desired fluid to be recirculated back to first concentrate valve 14a via second recirculation line 18s.

Any one or more or all of lines 18a to 18k, 18p and 18u, including any and all flexible pumping sections ps, may be durable, reusable and be made of a medically fluid safe metal, such as stainless steel, or any of the plastics listed herein, which are in one embodiment biocompatible, heat-disinfectable, and chemical-disinfectable.

In the illustrated embodiment of FIG. 1, each of pumps 12a to 12c, valves 14a to 14i, and heater 26 are powered and controlled via a control unit 50, which includes one or more processor 52, one or more memory 54 and a video controller 56 for controlling a video monitor 58. Video monitor 58 is part of an overall user interface 60 for each of systems 10a to 10c described herein. User interface 60 includes any one or more of a touch screen overlay operable with video monitor 58 and/or one or more electromechanical input device, e.g., membrane switches, for inputting information into control unit 50. Video monitor 58 and speakers (e.g., operable with a sound card of control unit 50) are provided to output information to the patient or user, e.g., alarms, alerts and/or voice guidance commands.

Similarly, each of conductivity sensors 22a to 22c, flow sensors 24a, 24b, temperature sensor 28, and pressure sensors 32a, 32b outputs to control unit 50. Control unit 50) uses the sensor outputs to control and monitor the components and their functions for each of systems described herein. Control unit 50 is programmed to run any of the flow sequences for systems 10a to 10c described herein. Control unit 50 may also include a transceiver and a wired or wireless connection to a network, e.g., the internet, for sending treatment data to and receiving prescription instructions from a doctor's or clinician's server interfacing with a doctor's or clinician's computer.

Control unit 50 uses the outputs from flow sensors 24a and 24b to know how much water and concentrate have been pumped by pumps 12a. 12b (sensor 24a) and used dialysis fluid has been pumped by pump 12c (sensor 24b). Because pumps 12a and 12b are mixing PD fluid, their speed may be controlled via feedback from conductivity sensor 22*a* and flow sensors 24*a*. The output from used PD fluid flow sensor 24*b* is used however to control the flowrate of used PD fluid pump 12*c* to pump at a desired or specified flowrate, controlling the power or input pulse train delivered to used dialysis fluid pump 12*c* to be varied as needed. The outputs from flow sensors 24*a* and 24*b* are also integrated over time to yield (i) how much fresh dialysis fluid is delivered to patient P, (ii) how much used dialysis fluid is removed from patient P, and (iii) a difference between (ii) versus (i) to know how much ultrafiltration ("UF") or excess water has been removed from the patient.

Control unit 50 causes inline heater 26 to heat fresh dialysis fluid from its starting temperature to body fluid temperature, e.g., 37° C., for comfortable delivery to patient P. The output from temperature sensor 28 located downstream from dialysis fluid heater 26 is used as feedback to control the amount of heating power supplied to heater 26. The feedback allows the target temperature to be reached without significant overshoot. If needed for this or any system embodiment discussed herein, an upstream temperature sensor (not illustrated) may be provided, e.g., between flow meter 24*a* and heater 26, for additional feedback, e.g., if incoming fluid to heater 26 is colder than usual then power to the heater is increased. Although not illustrated, an airtrap may be provided to remove air from the fresh dialysis fluid prior to patient delivery. Heating the dialysis fluid tends to separate dissolved air from the dialysis fluid. It is accordingly contemplated to locate the airtrap downstream from heater 26 in mixing line 18*k*.

Control unit 50 uses the output from conductivity sensor 22*a* to vary the speed of water pump 12*a* and concentrate pump 12*b* to arrive at a desired conductivity indicating that the PD fluid has been mixed properly, such as to known standard levels of 1.36% glucose PD fluid or 2.27% glucose PD fluid, or to some optimized glucose level that a clinician has determined and approved for the patient. System 10*a* allows for such optimization to occur. Control unit 50 in an embodiment uses the output from conductivity sensor 22*b* as a redundant and final check before allowing the PD fluid to be delivered to patient P. If for some reason the output from conductivity sensor 22*b* does not confirm that the PD fluid is suitable for patient delivery, then control unit 50 may cause fresh, downstream valve 14*f* to switch to allow the rejected PD fluid to be delivered to used PD fluid line 18*u* via first recirculation or bypass line 18*r*. The outputs from conductivity sensors 22*a* and 22*b* may be temperature compensated via the reading from temperature sensor 28. Control unit 50 may use the output from third or used PD fluid conductivity sensor 22*c* to interrogate used dialysis fluid to look for solute removal in the patient's effluent (e.g., for urea, $\beta_2$ microglobulin, and/or creatinine) or for signs of peritonitis.

Control unit 50 uses the output of fresh pressure sensor 32*a* as feedback to ensure that the positive pressure of fresh PD fluid delivered to patient P from pumps 12*a* and 12*b* is within a positive patient pressure limit (e.g., 3.0 psig (0.21 bar) or less). Control unit 50 uses the output of used pressure sensor 32*b* as feedback to ensure that the negative pressure of used PD fluid removed from patient P via pump 12*c* is within a negative patient pressure limit (e.g., at or between −1.5 psig (−0.10 bar) and zero psig). It should be appreciated that the order of the sensors in mixing line 18*k* and used dialysis fluid line 18*u* may be switched if desired.

Single First Concentrate Source Flow Arrangement

In a flow scenario in which first concentrate source 16*a* holds all necessary concentrates, e.g., electrolyte and glucose, control unit 50 in an embodiment fills patient P by (i) closing used PD fluid patient valve 14*h*, (ii) opening fresh PD fluid patient valve 14*g*, (iii) maintaining fresh, downstream valve 14*f* in a patient fill position, (iv) maintaining water valve 14*d* such that water pump 12*a* can pull purified water from purified water source 16*d*, and (v) manipulating valves 14*a* to 14*c* and 14*e* such that concentrate pump 12*b* can pull first concentrates (e.g., electrolyte and glucose) from source 16*a* through valves 14*a*, 14*b*, 14*c* and 14*e*. Control unit 50 uses the output from flow sensor 24*a* to maintain an overall desired flowrate or range (e.g., at or around 250 ml/min). Control unit 50 uses the output from first conductivity sensor 22*a* to apportion the overall flowrate between water pump 12*a* and concentrate pump 12*b* (e.g., adding to around 250 ml/min) to achieve a desired properly mixed conductivity, which is verified at redundant conductivity sensor 22*b*. Static mixer 20 ensures that water and concentrates are mixed homogeneously when reaching first conductivity sensor 22*a*. Control unit 50 uses the output from temperature sensor 28 to cause heater 26 to heat the mixed PD fluid to body temperature. Control unit 50 uses the output from pressure sensor 32*a* to ensure that a positive patient pumping pressure is within a preset pressure limit. When an integration of the output from flow sensor 24*a* indicates that a prescribed patient fill volume has been met, control unit 50 causes the patient fill from first concentrate source 16*a* to stop.

Single Second Concentrate Source Flow Arrangement

In a flow scenario in which second concentrate source 16*b* holds all necessary concentrates, e.g., electrolyte and glucose, control unit 50 in an embodiment performs the same procedure as described above for first concentrate source 16*a*, except that the states or positions of first concentrate valve 14*a* and second concentrate valve 14*b* are reversed. The state or position of first concentrate valve 14*a* is switched so that the port leading to first concentrate source 16*a* is closed. The state or position of second concentrate valve 14*b* is switched so that the port leading to second concentrate source 16*b* is opened.

Last Fill Concentrate Flow Arrangement

In a flow scenario in which last fill concentrate 16*c* holds all necessary concentrates, e.g., icodextrin concentrate, control unit 50 in an embodiment performs the same procedure as described above for first concentrate source 16*a*, except that the states or positions of first concentrate valve 14*a* and last fill valve 14*c* are reversed. The state or position of first concentrate valve 14*a* is switched so that the port leading to first concentrate source 16*a* is closed. The state or position of last fill valve 14*c* is switched so that the port leading to last fill concentrate 16*c* is opened.

Last Fill Fully Mixed Flow Arrangement

In a flow scenario in which last fill concentrate 16*c* holds a fully prepared last fill dialysis fluid, e.g., icodextrin, not just a last fill concentrate, control unit 50 in an embodiment maneuvers valves 14*a*, 14*b* and 14*d*, such that the ports to first concentrate source 16*a*, second concentrate source 16*a*, and purified water source 16*d* are closed, respectively. Valves 14*c* and 14*e* are positioned such that concentrate pump 12*b* can pull fully mixed last fill PD fluid from source 16*c* and pump same through static mixer 20 (where no mixing is needed), first conductivity sensor 22*a*, fresh PD fluid flow sensor 24*a*, inline heater 26, temperature sensor 28 and second conductivity sensor 22*b*. Control unit 50 closes used PD fluid patient valve 14*h*, opens fresh PD fluid patient valve 14*g*, and positions three-way fresh, downstream valve 14*f* such that heated, last fill PD fluid flows past pressure sensor 32*a*, through final or sterile stage filter 30, through internal fresh PD fluid patient line 18*p*, flexible patient line 40 and indwelling patient catheter 42 into the patient P's peritoneal cavity where the last fill PD fluid is allowed to dwell for a prolonged duration. Control unit 50 uses the output from flow sensor 24*a* to maintain an overall desired flowrate or range (e.g., at or around 250 ml/min). Control unit 50 uses the output from first conductivity sensors 22*a* and 22*b* to confirm the last fill PD fluid 16*c* meets the prescribed and expected PD fluid conductivity. Control unit 50 uses the output from temperature sensor 28 to cause heater 26 to heat the last fill PD fluid to body temperature. Control unit 50 uses the output from pressure sensor 32*a* to ensure that a positive patient pumping pressure is within a preset pressure limit. When an integration of the output from flow sensor 24*a* indicates that a prescribed patient fill volume has been met, control unit 50 causes the patient fill from last fill source 16*c* to stop.

First and Second Concentrate Source Flow Arrangement

In a flow scenario in which first concentrate source 16*a* holds a first needed concentrate, e.g., electrolyte, and second concentrate source 16*b* holds a second needed concentrate, e.g., glucose, control unit 50 in an embodiment fills patient P by (i) closing used PD fluid patient valve 14*h*, (ii) opening fresh PD fluid patient valve 14*g*. (iii) maintaining fresh, downstream valve 14*f* in a patient fill position, (iv) maintaining water valve 14*d* such that water pump 12*a* can pull purified water from purified water source 16*d*. (v) maintaining last fill valve 14*c* such that the port to last fill source 16*c* is closed, and (vi) manipulating valves 14*a*, 14*b* and 14*e* such that concentrate pump 12*b* selectively toggles and pulls either first concentrate (e.g., electrolyte) from source 16*a* through valves 14*a*, 14*b*, 14*c* and 14*e* or second concentrate (e.g., glucose) from source 16*b* through valves 14*b*, 14*c* and 14*e*. The first and second concentrates are mixed together and with purified water homogeneously at static mixer 20, after which fully prepared fresh PD is delivered to patient P. Control unit 50 uses the output from flow sensor 24*a* to maintain an overall desired flowrate or range (e.g., at or around 250 ml/min). Control unit 50 uses the output from first conductivity sensor 22*a* to apportion the overall flowrate between water pump 12*a* and concentrate pump 12*b* (e.g., adding to around 250 ml/min) to achieve a desired properly mixed conductivity, which is verified at redundant conductivity sensor 22*b*. Control unit 50 uses the output from temperature sensor 28 to cause heater 26 to heat the mixed PD fluid to body temperature. Control unit 50 uses the output from pressure sensor 32*a* to ensure that a positive patient pumping pressure is within a preset pressure limit. When an integration of the output from flow sensor 24*a* indicates that a prescribed patient fill volume has been met, control unit 50) causes the patient fill from first concentrate source 16*a* to stop.

In an alternative embodiment, it may be possible to finally mix fresh, heated PD fluid within patient P. Here, control unit 50 takes turns diluting either first or second concentrate from source 16*a* or 16*b* with purified water from purified water source 16*d* at static mixer 20. The conductivity of diluted first or second concentrate is confirmed at conductivity sensor 22*b*. The diluted first or second concentrate is then heated to body temperature via inline heater 26 and delivered at a desired flowrate via flow sensor 22*b*, the output of which is integrated so that a known volume of the diluted first or second concentrate is delivered to patient P. Control unit then performs the same procedure using the other of the first or second concentrate. The final mixture of fresh, heated PD fluid with the patient is therefore controlled volumetrically in one embodiment.

Drain Sequence

In any of the above-identified flow arrangements, after the patient fill is complete, control unit 50 allows the fresh PD fluid to dwell within patient P for a prescribed amount of time. Afterwards, or for an initial drain if the patient begins treatment full of effluent, control unit 50 drains the patient by closing PD fluid patient valve 14*g*, opening used PD fluid patient valve 14*h* and maintaining three-way fresh, downstream valve 14*f* and recirculation valve 14*i* in their normally open states. Control unit 50 causes used dialysis fluid pump 12*c* to pull used dialysis fluid from patient P at a safe negative pressure as monitored by used PD fluid pressure sensor 32*b* and at a desired flowrate as monitored by used PD fluid flow sensor 24*b*. The outputs from flow sensors 24*a* and 24*b* are integrated over time to yield (i) how much fresh dialysis fluid is delivered to patient P (sensor 24*a*), (ii) how much used dialysis fluid is removed from patient P (sensor 24*b*), and (iii) a difference between (ii) versus (i) to know how much ultrafiltration ("UF") or excess water has been removed from the patient. Control unit 50 may use the output from third or used PD fluid conductivity sensor 22*c* to interrogate used dialysis fluid to look for solute removal in the patient's effluent (e.g., for urea, $\beta_2$ microglobulin, and/or creatinine) or for signs of peritonitis. Used dialysis fluid is delivered to drain 34, e.g., a drain container or house drain.

First Disinfection Sequence Embodiment

Figure 2:
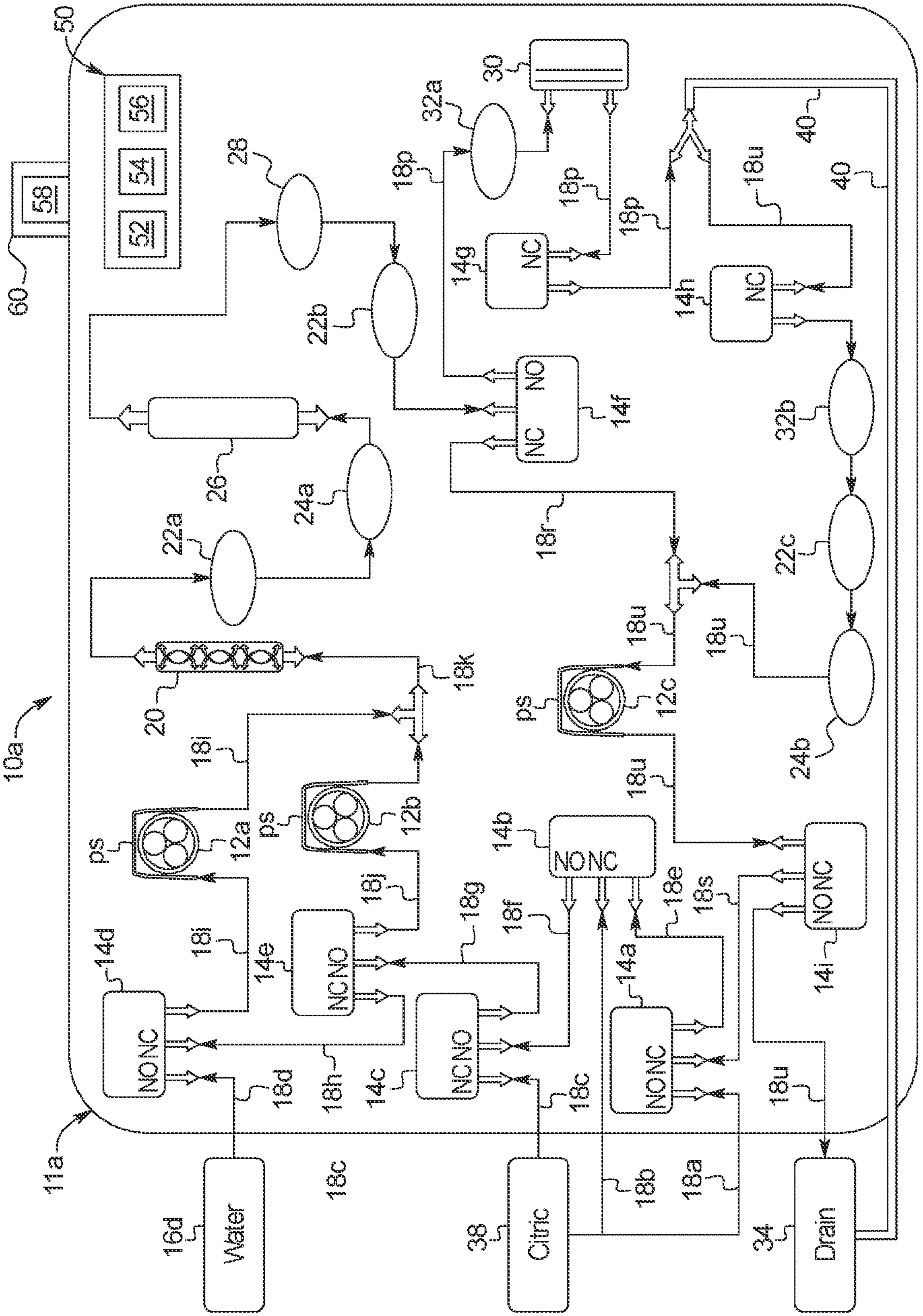
FIG. 2 is a flow schematic view of the first APD cycler embodiment showing one possible post-treatment disinfection arrangement.

Referring now to FIG. 2, one embodiment for performing a disinfection sequence at the end of treatment for any of systems 10*a* to 10*c* is illustrated. Here, at the end of treatment, control unit 50 via user interface 60 visually and/or audibly prompts patient P or a caregiver to disconnect flexible patient line 40 from indwelling patient catheter 42 or transfer set and connect that end of flexible patient line 40 to drain container or bag 34. If a house drain is used instead, or if it is desired not to include drain container or bag 34 in the disinfectant circuit or pathway, that end of flexible patient line 40 may be connected to the distal end of used dialysis fluid line 18*u* extending from recirculation valve 14*i*. The patient or caregiver is also prompted to remove concentrate sources 16*a* and 16*b* and last fill container 16*c* and to connect respective concentrate and last fill lines 18*a* to 18*c* instead to a source of disinfectant 38 (or to each other) to create a closed disinfection pathway. Source of disinfectant 38 may for example be a source of citric acid solution.

Once the closed disinfection circuit or pathway is formed, the patient or caregiver at user interface 60 may initiate a disinfection sequence in which control unit 50 causes the valve state of water valve 14*d* to be maintained so that the port to purified water source 16*d* is open to allow purified water to mix with the concentrated disinfectant from source 38. Water and concentrate pumps 12*a* and 12*b* are operated to pull disinfectant source of disinfectant 38. Used dialysis fluid pump 12*c* is operated to pull disinfectant through used dialysis fluid line 18*u*. Control unit 50 may reverse the flow direction of any one or more of pumps 12*a* to 12*c* one or more time during the disinfection sequence so that the disinfectant flows in a desired direction. Control unit 50 energizes inline heater 26 and uses the output of temperature sensor 28 to heat the disinfectant to a desired disinfecting temperature, e.g., 70° C. to 90° C., while the disinfectant is circulated throughout the closed disinfection circuit or pathway.

During the disinfection sequence, control unit 50 may cause (i) first concentrate valve 14*a* to be toggled to allow disinfect in from source 38 through first concentrate line 18*a* or disinfectant to flow through second recirculation line 18*s*, (ii) second concentrate valve 14*b* to be toggled to allow disinfectant to flow through line 18*f* or to allow disinfect in from source 38 through first concentrate line 18*a*, (iii) last fill valve 14*c* to be toggled to allow disinfectant to flow through line 18*g* or to allow disinfect in from source 38 through last fill line 18*c*, (iv) water valve 14*d* to be toggled to allow purified water to be pulled in from water purifier 16*d* via water line 18*d* or to allow disinfectant to flow through line 18*h*, water valve 14*d* and line 18*i*, (v) fresh, upstream valve 14*e* to be toggled to allow disinfectant to flow through lines 18*j* and 18*k* (and associated components) or to allow disinfectant to flow through lines 18*h* and 18*i*, (vi) fresh, downstream valve 14*f* to be toggled to allow disinfectant to flow through internal patient line 18*p* (and associated components) or to allow disinfectant to flow through recirculation lines 18*r*, (vii) fresh PD fluid patient valve 14*g* to be opened to allow disinfectant to flow through the remainder of patient line 18*p*, used dialysis fluid line 18*u* and/or flexible patient line 40 or to be closed to build pressure upstream of fresh PD fluid patient valve 14*g*, (viii) used PD fluid patient valve 14*h* to be opened to allow disinfectant to flow through used dialysis fluid line 18*u* or to be closed to force disinfectant through flexible patient line 40, and (ix) recirculation valve 14*i* to be toggled to allow disinfectant to flow through the distal portion of used dialysis fluid line 18*u* or to allow disinfectant to flow through second recirculation line 18*s*.

Control unit 50 causes the disinfection sequence to run for a predetermined and experimentally tested amount of time to ensure that all reusable lines and components of cycler 11*a* are properly sterilized for the next treatment. Again, semi-reusable final or sterile stage filter 30 is provided as additional protection for patient P. The disinfectant may be left within reusable lines and components of cycler 11*a* until the next treatment or be flushed at the end of the disinfection sequence. For flushing, control unit 50 in an embodiment toggles water valve 14*d* so that purified water may enter and be pumped through the reusable lines and components of cycler 11*a*.

In one preferred embodiment, a drain container 34 is provided, is reusable, e.g., be made of any of the plastics discussed above in rigid or semirigid form, and may be provided with wheels, a removably capped opening to pour out effluent, and a handle for performing same. Drain container accepts used dialysis fluid from multiple drains during treatment, including potentially an initial drain. Providing a drain container 34 is advantageous in one respect because a drain line running all the way to a house drain is not needed. At the end of treatment, user interface 60 prompts patient P to remove flexible patient line 40 from indwelling patient catheter 42 and to connect the flexible patient line 40 to a separate port provided at reusable drain container 34. Patient P is also prompted to remove concentrate sources 16*a* and 16*b* and last fill container 16*c* and to connect respective concentrate and last fill lines 18*a* to 18*c* instead to a source of disinfectant 38 as discussed above and shown in FIG. 2. Upon patient P confirming that the line switching is complete (the connection of flexible patient line 40 can additionally be confirmed automatically via a pressure check), control unit 50 causes machine or cycler 11*a* (or any of cyclers 11*a* to 11*c*) to fill all lines and components with a mixture of disinfectant and purified water as discussed above, wherein a desired composition of the mixture may be confirmed by one or more of conductivity sensors 22*a* to 22*c*. Filling the cycler with the disinfectant mixture also pushes or primes any fresh and/or used dialysis fluid remaining within the cycler to reusable drain container 34, which is made to be large enough to hold an entire treatment's used dialysis fluid plus the remaining fresh and used dialysis fluid.

User interface 60 next prompts patient P to remove a flexible portion of drain line 18*u* and flexible patient line 40 from reusable drain container 34 and to connect the flexible portion of drain line 18*u* and flexible patient line 40 together for performing the disinfection sequence discussed above. Here, advantageously, the disinfection sequence does not require the larger volume drain container 34 to be involved. While the disinfection sequence is being performed, or at any time before the next treatment, the patient or caregiver wheels or carries reusable drain container 34 to a toilet or bathtub and pours the prior treatment's effluent plus residual dialysis fluid flushed from the cycler at the end of treatment to drain. The disinfectant remains within cycler 11*a* (or any of cyclers 11*a* to 11*c*) until the next treatment in one embodiment.

At the beginning of the next treatment, user interface 60 prompts the patient to disconnect flexible patient line 40 from the flexible portion of drain line 18*u* and to connect those lines instead to their respective ports on reusable drain container 34 (which may be configured and oriented to minimize spillage). Upon the patient confirming such disconnection and reconnection at user interface 60 (which may be confirmed additionally automatically via a pressure check), control unit 50 causes cycler 11*a* (or any of cyclers 11*a* to 11*c*) to pump the disinfectant to reusable drain container 34 (which is made to be large enough to hold this extra volume as well). Reusable drain container 34 may include one or more hydrophobic vent that allows the lines and components of the cycler to be backfilled with filtered air vi an air purge, so that the patient can then remove source of disinfectant 38 and replace same with new concentrate sources 16*a* and 16*b* and last fill container 16*c* (as prompted by user interface 60), which may be connected to respective concentrate and last fill lines 18*a* to 18*c* without any or very little spillage. Control unit 50 then causes fresh dialysis fluid to be prepared and heated as described above and to be pumped so as to prime all lines and components of cycler 11*a* (or any of cyclers 11*a* to 11*c*). It should be appreciated that if source of disinfectant 38 can be removed and replaced with new concentrate sources 16*a* and 16*b* and last fill container 16*c* while respective concentrate and last fill lines 18*a* to 18*c* are filled with disinfectant and without any or very little spillage, the air purge backfilling just described is not needed. Instead, control unit 50 causes the newly prepared dialysis fluid to push or prime the disinfectant to reusable drain container 34, which is performed in one embodiment by pumping a sufficient volume of fresh dialysis fluid known to completely fill all lines and components of cycler 11*a* (or any of cyclers 11*a* to 11*c*). In either case, after the cycler is fully primed with fresh, heated dialysis fluid, user interface 60 prompts patient P to remove flexible patient line 40 from reusable drain container 34 and reconnect same to indwelling patient catheter 42 so that treatment may begin. It should be appreciated that a small amount of citric acid remaining in the cycler at the beginning of treatment is not harmful to the patient.

Second Disinfection Sequence Embodiment

Figure 3:
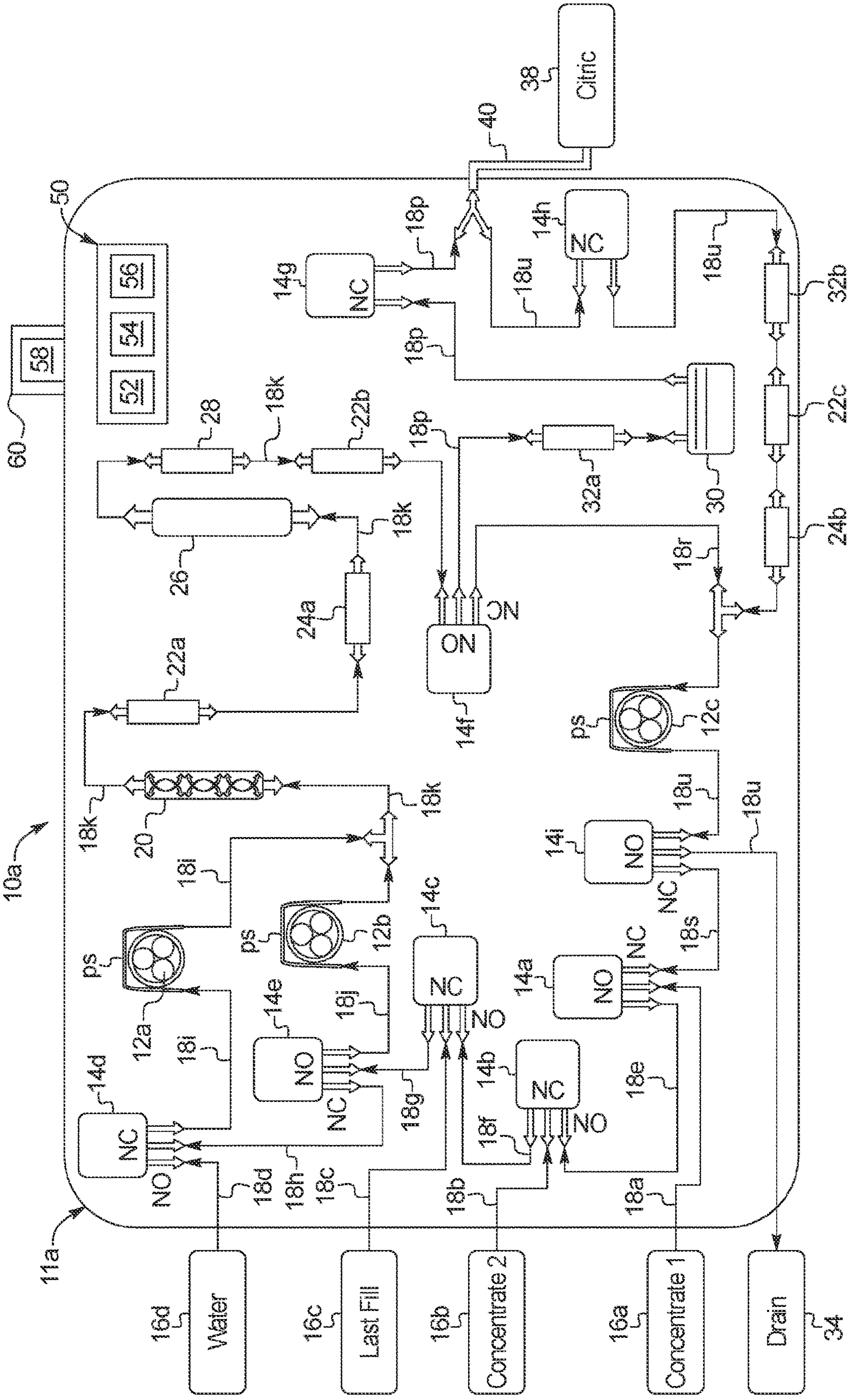
FIG. 3 is a flow schematic view of the first APD cycler embodiment showing a second possible post-treatment disinfection arrangement.

Referring now to FIG. 3, a second embodiment for performing a disinfection sequence at the end of treatment for any of systems 10*a* to 10*c* is illustrated. Here, at the end of treatment, control unit 50 via user interface 60 visually and/or audibly prompts patient P or a caregiver to disconnect flexible patient line 40 from indwelling patient catheter 42 or transfer set and connect that end of flexible patient line 40 to source of disinfectant 38. Concentrate sources 16*a* and 16*b* and last fill container 16*c* remain connected to machine or cycler 11*a* (or any of cyclers 11*a* to 11*c*). In one embodiment, at least flexible portions of the respective concentrate and last fill lines 18*a* to 18*c* are provided with and thus eventually discarded with concentrate sources 16*a* and 16*b* and last fill container 16*c*, so that they do not need to be disinfected. Here, control unit 50 causes valves 14*a* to 14*c* to be maintained in a position during the disinfection sequence to allow disinfectant to flow in either direction between valves 14*e* and 14*i*. Control unit 50 causes recirculation valve 14*i* to be maintained in a position during the disinfection sequence to allow disinfectant to flow in either direction between used PD fluid patient valve 14*h* and first concentrate valve 14*a*. Control unit 50 causes remaining valves 14*d*, 14*e*, 14*f*, 14*g* and 14*h* to be toggled as described above for the first disinfection sequence embodiment in any desired order or frequency. Control unit 50 may cause concentrated disinfectant, e.g., citric acid, to be pumped from the source of disinfectant 38 via any one or more of pumps 12*a* to 12*c*. The disinfectant is heated via inline heater 26 during the second disinfection sequence as described above to a desired disinfecting temperature, e.g., 70° C. to 90° C., and is circulated within the lines and components of the cycler for a predetermined and experimentally sufficient amount of time.

In an embodiment, control unit 50 at the end of the second disinfection sequence embodiment causes purified water from water purifier 16*d* to flush the disinfectant to drain 34 (container or house drain) by toggling recirculation valve 14*i* so that the disinfectant may leave cycler 11*a* (or any of cyclers 11*a* to 11*c*) via the distal end of used dialysis fluid line 18*u*. If drain 34 is a drain container it may be disposable like concentrate sources 16*a* and 16*b* and last fill container 16*c* or be reusable and include all the structure and functionality described above. If drain 34 is instead a drain line extending to a house drain, the drain line may likewise be disposable or possibly reusable, for example, if the drain line is sufficiently disinfected via the disinfectant being flushed through it. The purified water may in turn be flushed to drain 34 (container or house drain) via filtered air entering through a hydrophobic vent provided in water purifier 16*d*. Here, cycler 11*a* (or any of cyclers 11*a* to 11*c*) is left dry at the end of disinfection.

In an alternative embodiment, control unit 50 at the end of the second disinfection sequence embodiment allows the disinfectant to remain within cycler 11*a* (or any of cyclers 11*a* to 11*c*) until the start of the next treatment as described above for the first disinfection sequence embodiment. The disinfectant may then be flushed to drain 34 (container or house), e.g., with fresh, heated dialysis fluid as described above.

Whether the cycler is dry or wet at the beginning of treatment, cycler 11*a* (or any of cyclers 11*a* to 11*c*) may provide a hanger or place to store source of disinfectant 38 such that the end of flexible patient line 40 is at a proper location and orientation (e.g., vertical) for fully priming line 40. Once cycler 11*a* (or any of cyclers 11*a* to 11*c*) and flexible patient line 40 are fully primed, user interface 60 prompts the patient to remove flexible patient line 40 from source of disinfectant 38 and reconnect flexible patient line 40 to indwelling patient catheter 42 to begin a new treatment.

Second Cycler Embodiment

Figure 4:
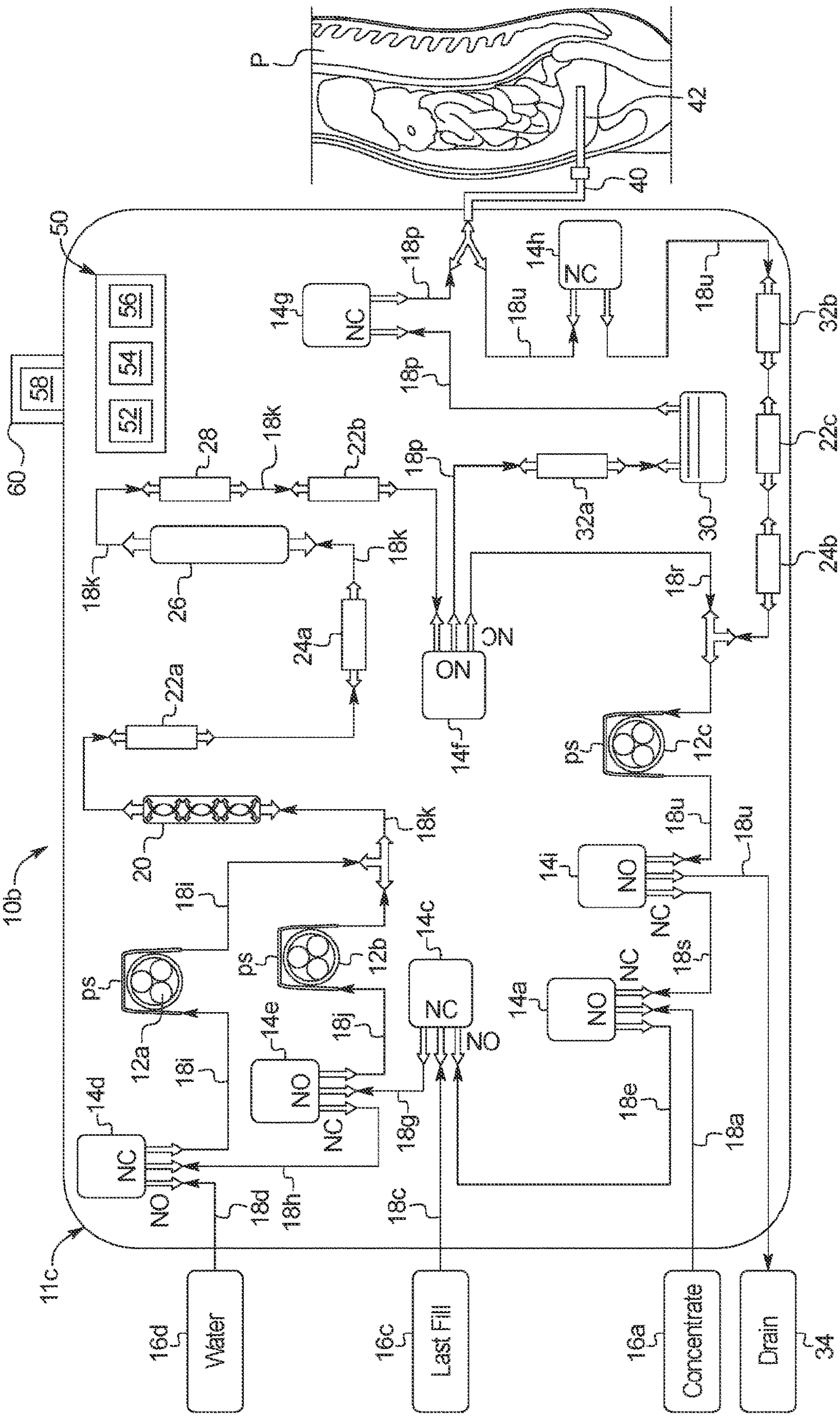
FIG. 4 is a flow schematic view of a second automated peritoneal dialysis ("APD") system of the present disclosure having online dialysis fluid generation using a single concentrate source and post-treatment disinfection.

Referring now to FIG. 4, a second primary embodiment of an automated peritoneal dialysis ("APD") system 10*b* and associated methodology of the present disclosure includes an APD machine or cycler 11*b* under control of control unit 50, which is generally defined by the rectangular box in FIG. 4. In the illustrated embodiment, APD machine or cycler 11*b* includes many of the same components as discussed above for cycler 11*a* of system 10*a*. Those components are numbered the same as above for system 10*a* and include all of the structure, functionality and alternatives discussed above for cycler 11*a* of system 10*a*. The primary difference with system 10*b* is that cycler 11*b* operates with a single first concentrate source 16*a*, which is again connected to first concentrate valve 14*a* via first concentrate line 18*a*. Second concentrate source 16*b*, second concentrate valve 14*b* and second concentrate line 18*b* are not provided. Line 18*f* is likewise not needed or provided. Last fill container 16*c* connected to last fill valve 14*c* via last fill line 18*c* are provided again, wherein fill container 16*c* may hold a last fill concentrate (e.g., icodextrine concentrate) for mixing with purified water or may hold a fully mix last fill PD fluid (e.g., fully mixed icodextrine).

Each necessary concentrate (e.g., glucose and electrolyte) is provided with single source of concentrate 16*a* in system 10*b*, where again the concentrates may be separated via a peel seal prior to treatment. The patient or caregiver breaks or ruptures the peel seal prior to treatment to allow the concentrates to mix at least initially prior to being removed from first source of concentrate 16*a*. First source of concentrate 16*a* holds multiple fill volume's worth of concentrate in one embodiment.

Fresh dialysis fluid is prepared online or at the time of use and delivered to patient P as described above at "Single First Concentrate Source Flow Arrangement", except that second concentrate source 16*b*, second concentrate valve 14*b*, second concentrate line 18*b* and line 18*f* are not provided or involved. A last fill may be provided by system 10*b* as described above at "Last Fill Concentrate Flow Arrangement" or as described above at "Last Fill Fully Mixed Flow Arrangement", except that second concentrate source 16*b*, second concentrate valve 14*b*, second concentrate line 18*b* and line 18*f* are not provided or involved. System 10*b* may drain patient P as described above at "Drain Sequence", except that second concentrate source 16*b*, second concentrate valve 14*b*, second concentrate line 18*b* and line 18*f* are not provided or involved. System 10*b* may provide a disinfection sequence as described above at "First Disinfection Sequence Embodiment" (FIG. 2) or "Second Disinfection Sequence Embodiment" (FIG. 3), except that second concentrate source 16*b*, second concentrate valve 14*b*, second concentrate line 18*b* and line 18*f* are not provided or involved.

Third Cycler Embodiment

Figure 5:
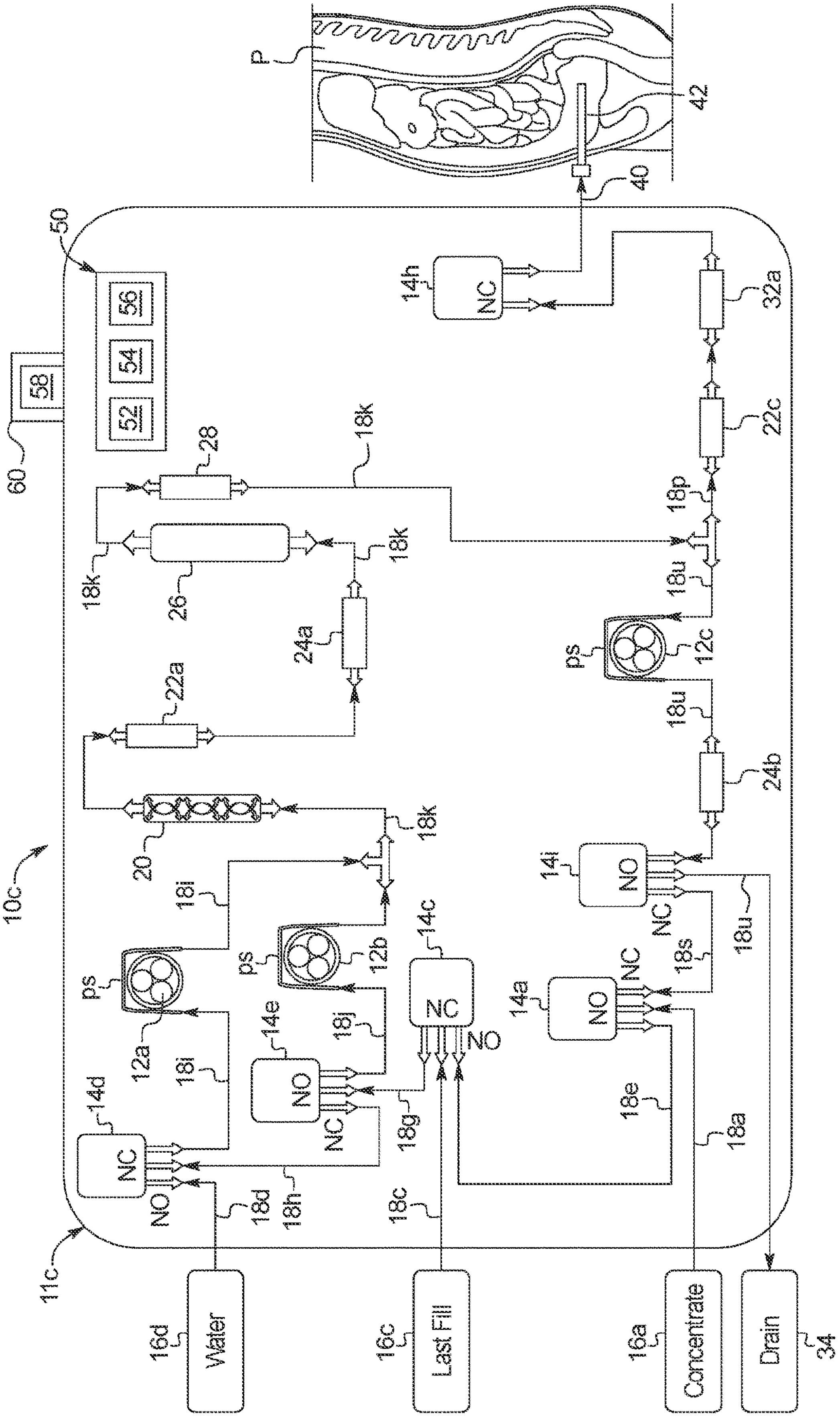
FIG. 5 is a flow schematic view of a third automated peritoneal dialysis ("APD") system of the present disclosure having online dialysis fluid generation using a single concentrate source and post-treatment disinfection, and wherein the fluid circuitry is simplified.

Referring now to FIG. 5, a third primary embodiment of an automated peritoneal dialysis ("APD") system 10*c* and associated methodology of the present disclosure includes an APD machine or cycler 11*c* under control of control unit 50, which is generally defined by the rectangular box in FIG. 5. In the illustrated embodiment, APD machine or cycler 11*c* includes many of the same components as discussed above for cycler 11*a* of system 10*a*. Those components are numbered the same as above for system 10*a* and include all of the structure, functionality and alternatives discussed above for cycler 11*a* of system 10*a*. The primary differences with system 10*c* are that, like system 10*b*, only a single first source of concentrate 16*a* is provided and cycler 11*c* is simplified such that internal patient line 18*p* handles both fresh dialysis fluid delivered to patient P and used dialysis fluid removed from patient P. This change enables three-way fresh, downstream valve 14*f* and one of two-way fresh or used PD fluid patient valves 14*g* or 14*h* (used valve 14*h* shown as being removed) to be eliminated. Also, only a single fresh PD fluid conductivity sensor 22*a* is needed (conductivity sensor 22*b* eliminated) along with used PD fluid conductivity sensor 22*c*. Further, only a single pressure sensor 32*a* is needed, which is located just ahead of PD fluid patient valve 14*g* so as to be able to measure both positive and negative pressures associated with fresh dialysis fluid delivery to and used dialysis fluid removal from, respectively, patient P. First recirculation line 18*r* is also eliminated. Mixing line 18*k* instead "T's" or "Y's" together with internal patient line 18*p* and used dialysis fluid line 18*u* to enable fluid to be recirculated if needed.

Semi-reusable final or sterile stage filter 30 is also illustrated as being eliminated, which is possible with any of systems 10*a* to 10*c* if the disinfection sequences described herein are found to be effective enough that the filter is not needed. Cycler 11*c* of system 10*c* may provide final or sterile stage filter 30 if it is found to be needed. Filter 30 would then be installed and be replaceable according to any of the alternative discussed herein. Final or sterile stage filter 30 may be located in mixing line 18*k* just ahead of the "T" or "Y" with internal patient line 18*p* and used dialysis fluid line 18*u* if, for example, it is desirable for the filter not to see used dialysis fluid or effluent, which may unduly clog the filter. If clogging is not an issue, final or sterile stage filter 30 could be placed instead in internal patient line 18*p*, e.g., between conductivity sensor 22*c* and pressure sensor 32*a* so that the output of pressure sensor 32*a* takes into account pressure drop through filter 30 for a patient fill and sees the negative pressure prior to filter 30 for a patient drain.

Conductivity sensor 22*a* outputs to control unit 50 and may be used to monitor and control mixing between first source of concentrate 16*a* and purified water from source of purified water 16*d* and possible between last fill concentrate 16*c* and purified water as described above. Flow sensors 24*a* and 24*b* output to control unit 50 and are used as described above to set fresh and used PD fluid flowrates and for monitoring and controlling amounts of (i) fresh PD fluid delivered to patient P for a patient fill, (ii) used PD fluid removed from patient P for a patient drain, and (iii) UF removed from patient P by subtracting (i) from (ii). In an alternative embodiment for cycler 11*c* of system 10*c*, a single flow sensor (24*a* or 24*b*) is provided in patient line 18*p* for measuring the flow of both fresh and used dialysis fluid, the output from which control unit 50 uses to set fresh and used PD fluid flowrates and for monitoring and controlling the amount (i) to (iii). The output from temperature sensor 28 (upstream temperature sensor could be provided in addition) is used to control inline heater 26 as described above. The output from conductivity sensor 22*c* may be used to interrogate used dialysis fluid to look for solute removal in the patient's effluent (e.g., for urea, 2 microglobulin, and/or creatinine) or for signs of peritonitis as described above. Outputs from pressure sensor 32*a* are used by control unit 50 to ensure that (i) the positive pressure of fresh PD fluid delivered to patient P from pumps 12*a* and 12*b* is within a positive patient pressure limit (e.g., 3.0 psig (0.21 bar) or less) and (ii) the negative pressure of used PD fluid removed from patient P via pump 12*c* is within a negative patient pressure limit (e.g., at or between −1.5 psig (−0.10 bar) and zero psig).

As with system 10*b*, each necessary concentrate (e.g., glucose and electrolyte) is provided with single source of concentrate 16*a* in system 10*c*, where again the concentrates may be separated via a peel seal prior to treatment. The patient or caregiver breaks or ruptures the peel seal prior to treatment to allow the concentrates to mix at least initially prior to being removed from first source of concentrate 16*a*. First source of concentrate 16*a* holds multiple fill volume's worth of concentrate in one embodiment. It should be however that system 10*c* may alternatively include second source of concentrate 16*b*, second concentrate valve 14*b* and the associated lines be provided additionally in combination with the dual direction internal patient line 18*p* and the associated valve and sensor reduction of cycler 11.

Fresh dialysis fluid is prepared online or at the time of use and delivered to patient P by system 10*c* as described above at "Single First Concentrate Source Flow Arrangement", except that second concentrate source 16*b*, valves 14*b*, 14*f*, 14*h*, lines 18*b*, 18*f*, 18*r*, conductivity sensor 22*b* and pressure sensor 32*b* may not be provided or involved. A last fill may be provided by system 10*c* as described above at "Last Fill Concentrate Flow Arrangement" or as described above at "Last Fill Fully Mixed Flow Arrangement", except that second concentrate source 16*b*, valves 14*b*, 14*f*, 14*h*, lines 18*b*, 18*f*, 18*r*, conductivity sensor 22*b* and pressure sensor 32*b* may not be provided or involved. System 10*c* may drain patient P as described above at "Drain Sequence", except that second concentrate source 16*b*, valves 14*b*, 14*f*, 14*h*, lines 18*b*, 18*f*, 18*r*, conductivity sensor 22*b* and pressure sensor 32*b* may not be provided or involved. System 10*c* may provide a disinfection sequence as described above at "First Disinfection Sequence Embodiment" (FIG. 2) or "Second Disinfection Sequence Embodiment" (FIG. 3), except that second concentrate source 16*b*, valves 14*b*, 14*f*, 14*h*, lines 18*b*, 18*f*, 18*r*, conductivity sensor 22*b* and pressure sensor 32*b* may not be provided or involved.

It should be understood that various changes and modifications to the presently preferred embodiments described herein will be apparent to those skilled in the art. For example, while the fluid schematics illustrated herein show connections to specific NO and NC ports of valves 14*a* to 14*f* and 14*i* forming one workable overall flow schematic, the present disclosure is not limited to the specific NO and NC connections, and those of skill may determine others. Also, while a combined chemical and heat disinfection is disclosed, chemical or heat alone may be sufficient. Other types of disinfection, e.g., ultraviolet light, may be used additionally or alternatively. Further, control unit 50 for any of systems 10*a* to 10*c* may be programmed to end a patient drain when (i) a prescribed amount of used dialysis fluid (e.g., a factor such as 1.3 multiplied by the prescribed fill volume) has been removed from the patient or (ii) a characteristic signal or output from pressure sensor 22*c*, e.g., characteristic negative pressure increase, is seen at control nit 50, which indicates that the patient is empty or virtually empty. Moreover, while flow sensing for flowrate and integration for volume control is disclosed, inherently accurate pumps, such as piston pumps, or volumetric control components, such as balance chambers, may be used instead. Still further, the order and location of the sensors described herein may be varied. For example, fresh PD fluid flow sensor 24*a* may be located along and operate with mixing line 18*k* or patient line 18*p* in systems 10*a* and 10*b*. Further additionally, it is contemplated for control unit 50 to rinse leftover fresh and/or used PD fluid within the lines and components of cycler 11*a* to 11*c* to drain (container or house) using purified water from source of purified water 16*d* prior to introducing disinfectant from source of disinfectant 38 into the cycler. It is therefore intended that any or all of such changes and modifications may be covered by the appended claims.

The invention is claimed as follows:

1. A peritoneal dialysis ("PD") machine comprising:
a water pump;
a concentrate pump;
a water valve located upstream of the water pump, and an inlet to the water valve positioned to receive purified water;
a concentrate valve located upstream of the concentrate pump, and an inlet to the concentrate valve positioned to receive PD fluid concentrate;
a mixing line located downstream from the water pump and the concentrate pump;
a conductivity sensor positioned to sense a mixture of the purified water and the PD fluid concentrate that at least partially forms fresh PD fluid;
a flexible patient line configured to bring the at least partially formed fresh PD fluid to a patient and remove used PD fluid from the patient; and
a control unit configured to control the water pump, the concentrate pump, the water valve and the concentrate valve, the control unit also configured to receive an output from the conductivity sensor, the control unit further configured to run a disinfection sequence in which an end of the flexible patient line is directly connected to an external container of a disinfectant concentrate to receive disinfectant instead of being connected to the patient.

2. The PD machine of claim 1, which further includes a used PD fluid line, and wherein the used PD fluid line is placed in fluid communication with a drain container or a house drain.

3. The PD machine of claim 2, wherein during treatment, the used PD fluid line is placed in fluid communication with the drain container or the house drain.

4. The PD machine of claim 2, wherein the drain container is a reusable container.

5. The PD machine of claim 2, which includes a used dialysis fluid pump operable with the used PD fluid line.

6. The PD machine of claim 5, wherein at least one of the water pump, the concentrate pump, or the used dialysis fluid pump is operated in at least one direction during the disinfection sequence.

7. The PD machine of claim 1, which includes a final or sterile stage filter positioned and arranged to filter the at least partially formed fresh PD fluid prior to delivery to the patient.

8. The PD machine of claim 7, wherein the final or sterile stage filter is at least one of a reusable filter or an ultrafilter.

9. The PD machine of claim 1, which includes a mixer located along the mixing line.

10. The PD machine of claim 1, which includes a heater, and wherein the control unit is further configured to cause the heater to heat the disinfectant during the disinfection sequence.

11. The PD machine of claim 10, wherein the heater is an inline heater.

12. The PD machine of claim 1, which includes an internal patient line positioned to deliver (a) the at least partially formed fresh PD fluid to the flexible patient line, wherein a used dialysis fluid line receives the used PD fluid from the flexible patient line, or (b) the at least partially formed fresh PD fluid to the flexible patient line and receive the used PD fluid from the flexible patient line.

13. The PD machine of claim 12, wherein in option (a), a fresh PD fluid pressure sensor is operable with the internal patient line and a used PD fluid pressure sensor is operable with the used dialysis fluid line, or in option (b), a fresh and used PD fluid pressure sensor is operable with the internal patient line.

14. The PD machine of claim 12, wherein in option (a), the conductivity sensor is operable with the mixing line and a second conductivity sensor is operable with the used dialysis fluid line, or in option (b), the conductivity sensor is operable with the mixing line and a second conductivity sensor is operable with the internal patient line.

15. The PD machine of claim 14, wherein the control unit is configured to:
use the output from the conductivity sensor for feedback in mixing the purified water and the PD fluid concentrate; and
use a second output from the second conductivity sensor for evaluating the used PD fluid removed from the patient.

16. The PD machine of claim 12, wherein in option (a), a first flow sensor is operable with the mixing line or the internal patient line and a second flow sensor is operable with the used dialysis fluid line, or in option (b), a first flow sensor is operable with the mixing line and a second flow sensor is operable with the used dialysis fluid line, or in option (b), a single flow sensor is operable with the internal patient line.

17. The PD machine of claim 16, wherein the control unit is configured to use outputs from the first and second flow sensors or the single flow sensor to at least one of (i) control a flowrate of the at least partially formed fresh PD fluid, (ii) control a flowrate of the used PD fluid, (iii) determine an amount of the at least partially formed fresh PD fluid delivered to the patient, (iv) determine an amount of the used PD fluid removed from the patient, or (v) determine an amount of ultrafiltration ("UF") removed from the patient.

18. The PD machine of claim 1, wherein the control unit is configured to cause a performance of at least one of (a) a purified water rinse of any remaining amount of the at least partially formed fresh PD fluid and/or the used PD fluid prior to introduction of the disinfectant, (b) a rinse of any remaining amount of the at least partially formed fresh PD fluid and/or the used PD fluid using the disinfectant, (c) a purified water rinse of the disinfectant after the disinfection sequence, or (d) a filtered air purge after the disinfection sequence.

19. The PD machine of claim 1, wherein the concentrate valve is a first concentrate valve and the PD fluid concentrate is a first PD fluid concentrate, and which includes a second concentrate valve under control of the control unit, the second concentrate valve located upstream of the concentrate pump, and an inlet to the second concentrate valve positioned to receive a second PD fluid concentrate, and wherein the control unit is further configured to manipulate the first and second concentrate valves and control the concentrate pump so as to (i) mix the first PD fluid concentrate or the second PD fluid concentrate with the purified water or (ii) mix the first PD fluid concentrate and the second PD fluid concentrate with the purified water.

20. The PD machine of claim 19, wherein in option (ii), the mixture of the first PD fluid concentrate, the second PD fluid concentrate, and the purified water forms a final fresh PD fluid that is mixed in the mixing line or in the patient.

* * * * *